US005649664A

United States Patent [19]

Brass et al.

[11] Patent Number: 5,649,664

[45] Date of Patent: Jul. 22, 1997

[54] REUSABLE SPRAYER

[75] Inventors: Richard Brass, Reinbeck, Iowa; Raymond F. Cracauer, Plymouth; Roland Beihl, Invergrove Heights, both of Minn.; Robert C. Hudson, Jr., Northbrook, Ill.

[73] Assignee: H.D.Hudson Manufacturing Company, Chicago, Ill.

[21] Appl. No.: 416,147

[22] Filed: Apr. 4, 1995

[51] Int. Cl.[6] .............................. B05B 9/08; A61M 11/02

[52] U.S. Cl. .......................... 239/373; 239/154; 222/401; 251/353

[58] Field of Search .................................. 239/337, 373, 239/152, 154, 583, 569, 541, 579, 530; 222/401, 402, 530, 538; 220/675, 609, 608, 289; 251/353, 349

[56] References Cited

U.S. PATENT DOCUMENTS

| | | | |
|---|---|---|---|
| 2,457,993 | 1/1949 | Fletcher et al. | 239/583 X |
| 3,002,698 | 10/1961 | Gallo | 239/583 X |
| 3,129,278 | 4/1964 | Santarelli | 239/583 X |
| 3,343,795 | 9/1967 | Pinke | 239/152 |
| 3,670,966 | 6/1972 | Korda | 239/583 X |
| 3,993,245 | 11/1976 | Smith | 239/154 X |
| 4,124,674 | 11/1978 | Jones et al. | 222/401 X |
| 4,128,209 | 12/1978 | Johnson | 239/583 |
| 4,154,367 | 5/1979 | Hanson et al. | 222/401 X |
| 4,489,914 | 12/1984 | Stevenson et al. | 251/353 X |
| 4,801,088 | 1/1989 | Baker | 239/152 |
| 4,805,814 | 2/1989 | Allen Sr. | 222/538 |
| 5,072,884 | 12/1991 | Ellison et al. | 239/373 |
| 5,301,877 | 4/1994 | Madison | 239/154 |
| 5,472,124 | 12/1995 | Martushev | 222/530 X |
| 5,478,015 | 12/1995 | Black | 239/154 |

FOREIGN PATENT DOCUMENTS

| | | | |
|---|---|---|---|
| 678547 | 1/1964 | Canada | 239/333 |
| 716431 | 8/1965 | Canada | 239/333 |
| 9172 | of 1889 | United Kingdom | 239/333 |
| 787585 | 12/1957 | United Kingdom | 251/353 |

*Primary Examiner*—Lesley D. Morris
*Attorney, Agent, or Firm*—Kane, Dalsimer, Sullivan, Kurucz, Levy, Eisele and Richard, LLP

[57] ABSTRACT

A sprayer includes a tank for liquid, a pump for pressurizing the liquid, a hose for the liquid under pressure and a manually activated spray control valve coupled with the hose and upon digitally sliding a valve body a valve plug is adapted to engage a valve seat to close the valve and disengage the valve seat to open the valve.

11 Claims, 4 Drawing Sheets

REUSABLE SPRAYER

BACKGROUND OF THE INVENTION

Garden and industrial sprayers are normally completely reusable and feature a pressure tank for the liquid solution to be dispensed having a sealable fill opening,an internally mounted piston/cylinder pump for pressurizing the tank interior, an outlet hose, a flow control valve associated with the hose, and an extension rod having a discharge nozzle. The tank is usually filled with the desired chemical in concentrated form which is diluted by adding water to arrive at the desired solution for spraying. The chemical concentrate is purchased commercially from the desired source and may be contained in 1 gallon, 5 gallon or higher capacity bottles or containers.

SUMMARY OF THE INVENTION

A principal object of the present invention is to provide a cost effective reusable sprayer that may be provided prefilled and sold and purchased as a complete filled package including a built in pump, outlet hose, spray control valve, rod extension and discharge nozzle.

Another object is to provide a sprayer of the foregoing type that is relatively easy to manufacture and which possesses a tank similar in appearance to the commercially available bottles or containers for chemical concentrates.

Other objects and advantages will become apparent from the following detailed description which is to be taken in conjunction with the accompanying drawings.

DETAILED DESCRIPTION

Figure 2:
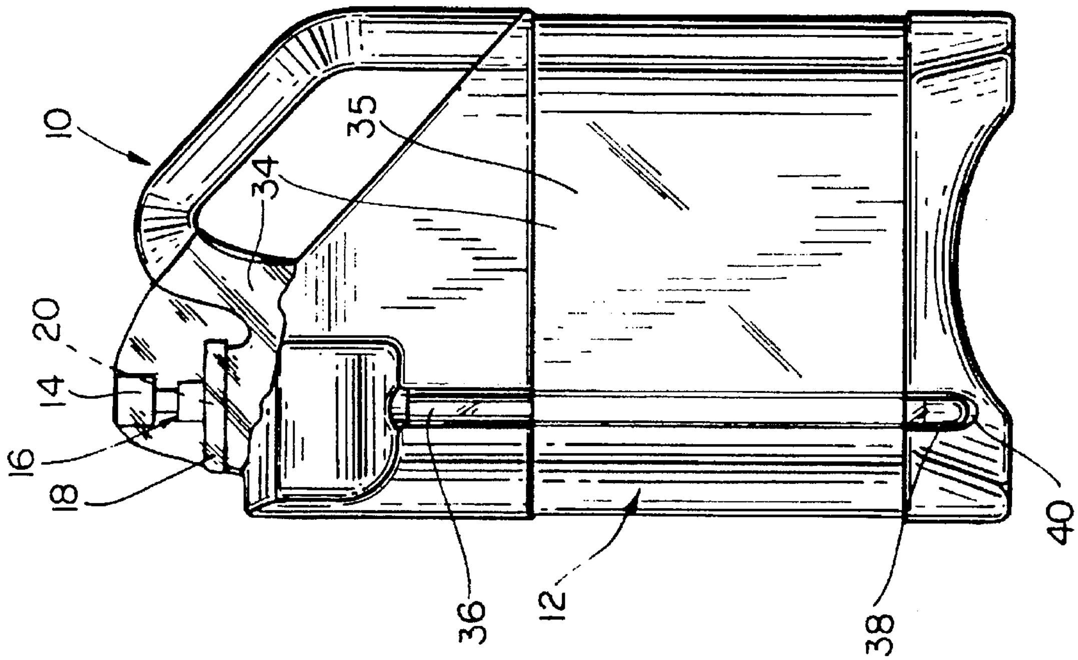
FIG. 2 is a rear elevational view thereof.
Figure 1:
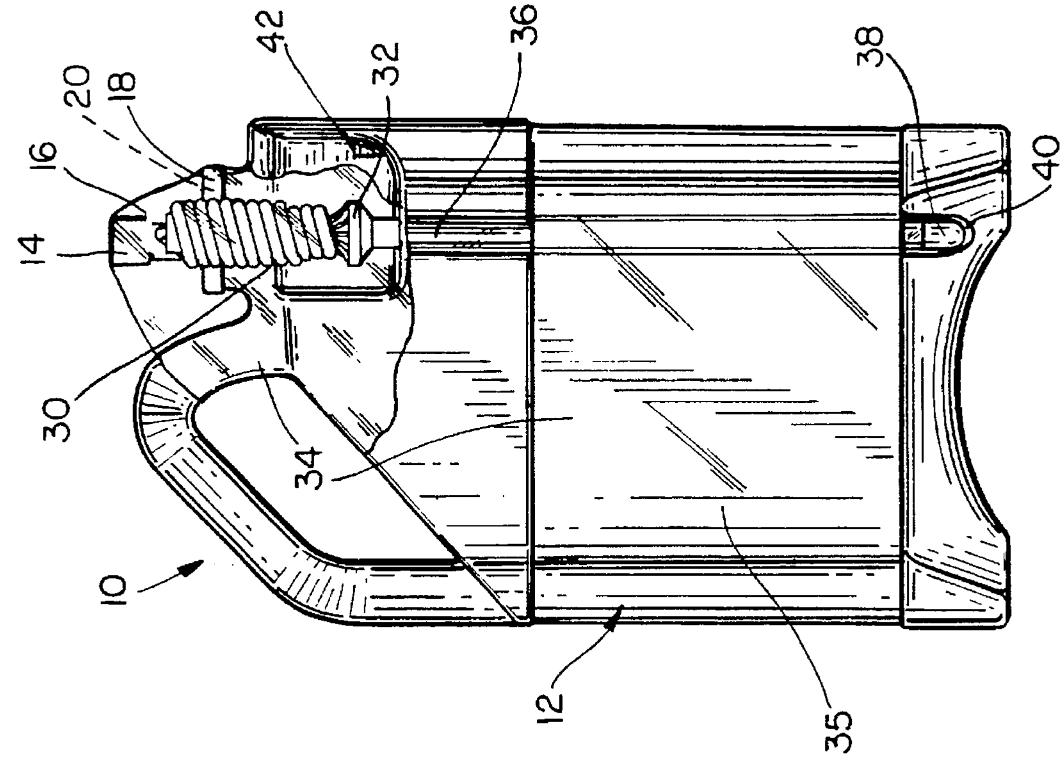
FIG. 1 is a front elevational view of the sprayer of this invention as commercially sold.
Figure 3:
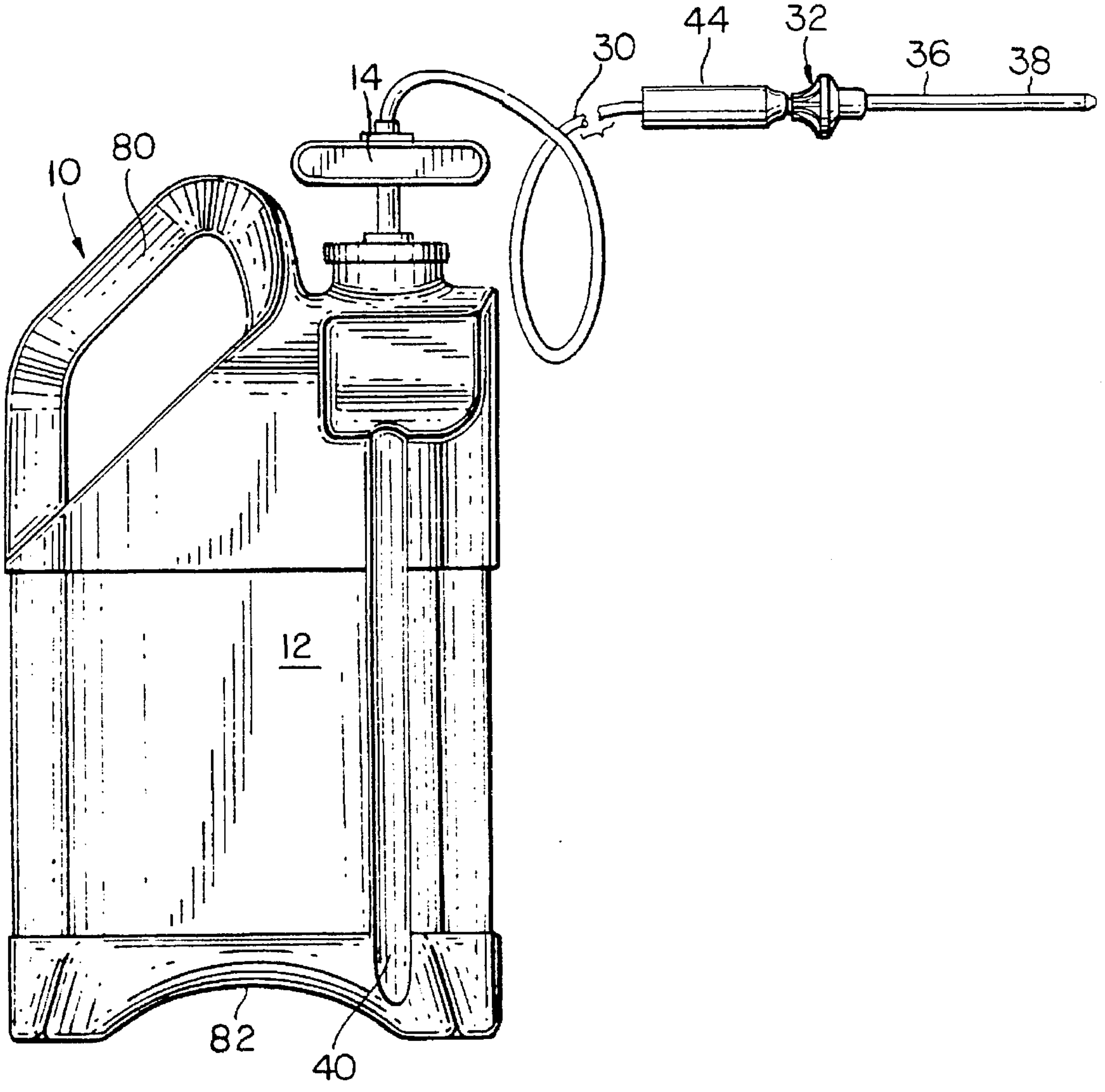
FIG. 3 is a front elevational view of the sprayer ready for use.
Figure 4:
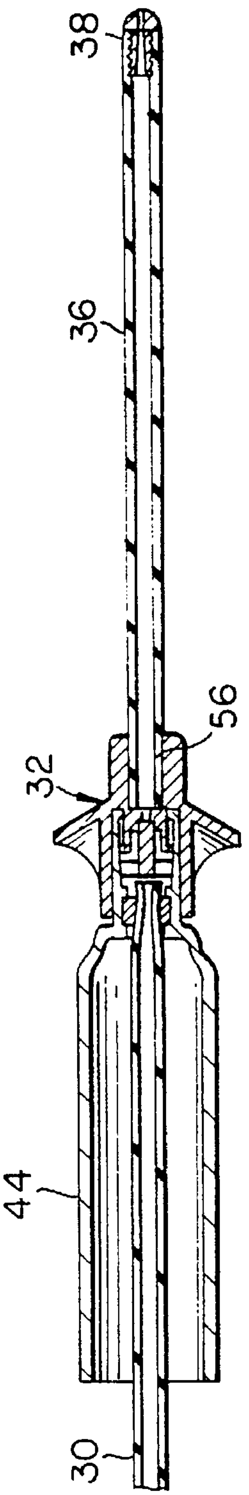
FIG. 4 is an enlarged fragmentary view of the handle and extension rod with discharge nozzle and the interposed spray control valve.
Figure 6:
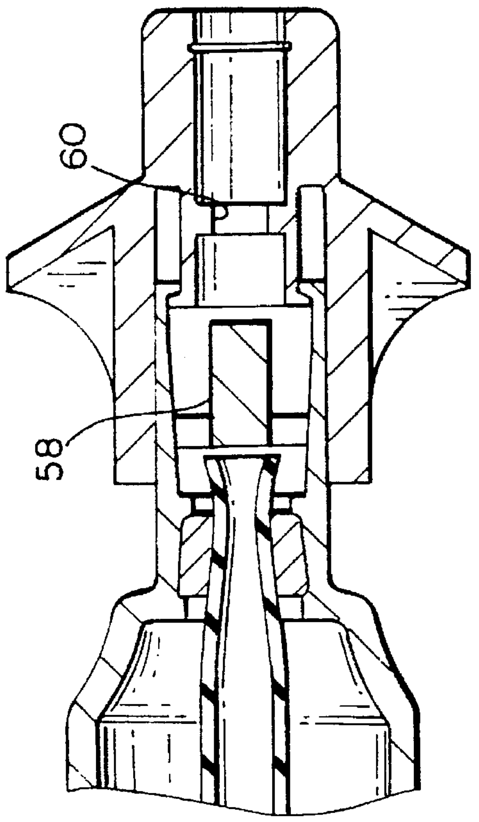
FIG. 6 is a similar view with the spray control valve open.

In the drawing, the sprayer package 10 as supplied to the consumer is illustrated in FIGS. 1 and 2. In this condition the tank 12 of a suitable plastic is not pressurized but contains the diluted chemical solution to be sprayed and is also suitably sealed so as to be a so called "shipper". Towards this end, the pump handle 14 will be suitably releasably secured in place for example, by tape, shrink wrap or any suitable releasable clip or fastener. The pump assembly 16 and, specifically, the top cap 18 on the pump cylinder will be suitably sealed and secured to the tank 12 across a fill opening 20 but only after the tank 12 is filled. In this regard, the tank 12, may be formed by blow molding from a suitable resin.

The hose 30 and spray control valve 32 may be conveniently sealably secured to the pump handle 14 and all are placed as shown and perhaps secured in place by tape, shrink wrap or other suitable fastening means. The shrink wrap label 34 extending circumferentially around the tank 12 within the circumferential recess 35 conveniently secures the extension rod 36 and discharge nozzle 38 within the longitudinal cavity 40. Thus, the sprayer package 10 depicted in FIGS. 1 and 2 will be marketed and sold as shown with a contained chemical, preferably not under pressure, ready for spraying in the same fashion as and along with bottles of such solution or chemical concentrate.

Once the sprayer package 10 is purchased, the consumer prepares it for spraying by removing the fastening means holding the pump handle 14, hose 30 and control valve 32 and then freeing extension rod 36 and nozzle 38. The pump assembly 16 is then activated.

Referring now to pump assembly 16, it will be understood that the pump assembly is disposed internally of the tank 12 and may be of the type that pressurizes the tank interior as disclosed in commonly assigned U.S. patent application Ser. No. 08/416,137 filed concurrently herewith and entitled "One Time Use, Non-Reusable Sprayer" and now U.S. Pat. No. 5,609,272 or of the type that pressurizes the pump cylinder as disclosed in commonly assigned U.S. patent application Ser. No. 08/416,228 filed concurrently herewith and entitled "Limited Time Use Sprayer." In either event, liquid under pressure from the tank 12 will be forced into hose 30 for spraying out its nozzle 38 under the control of valve 32.

Figure 5:
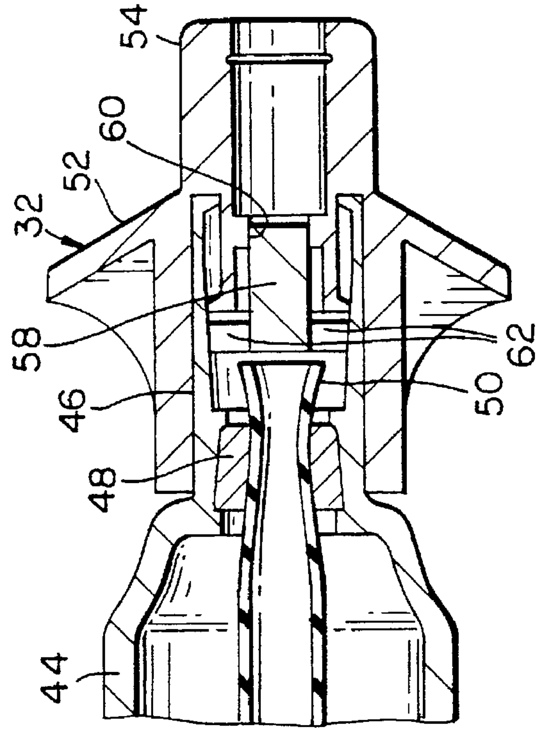
FIG. 5 is an enlarged fragmentary sectional view of an embodiment of the spray control valve in its closed position.

The valve 32 is advantageously selected for its simplicity of structure and operation and manipulation with a single hand from a closed position to an open position back to a closed position. This valve 32 is conveniently located at the distal end of handle 44 and is adapted to be manipulated digitally by the fingers of the hand holding the handle 44. The distal end of handle 44 includes a reduced cylindrical boss 46 and mounts internally a resilient retainer or clamping ring 48 for tightley clamping and securing the distal end 50 of hose 30. Slidable on the exterior of cylindrical boss 46 is valve body 52, the distal end 54 of which mounts the proximal end 56 of extension rod 36. Also mounted internally of cylindrical boss 46 is a valve plug 58 which is adapted to seat in and close the valve seat 60 when the valve body 52 is retracted to this valve closed position as shown in FIG. 5. Liquid flow from the base of hose 30 to the extension rod 36 when the valve 32 is opened is facilitated by openings 62. When it is desired to open the flow control valve 32, the valve body is digitally moved axially forwardly to retract the plug 58 from the valve seat 60, thereby permitting liquid under pressure to be discharged out through the nozzle 38. The valve 32 is closed by simply digitally retracting the valve body 52 to dispose plug 58 in valve seat 60.

An angled handle 80 extends upwardly and integrally with the tank 12. When the handle 80 is gripped, the tank will tilt to permit all of the liquid in the tank to be removed by spraying. The tank 12 has a base having a reverse dome 82 integrally molded in the base for strengthening the base and prevent ballooning thereof.

Figure 7:
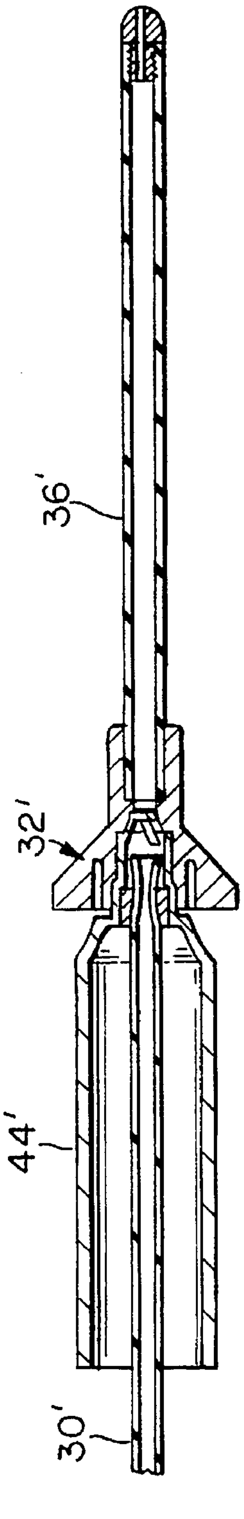
FIG. 7 is a view similar to FIG. 4 of a somewhat preferred version of the spray control valve.
Figure 9:
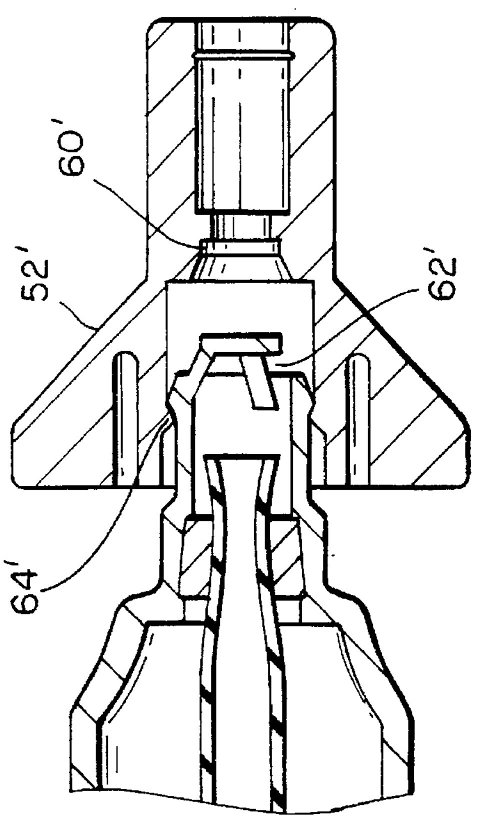
FIG. 9 is a similar view with the spray control valve open.
Figure 8:
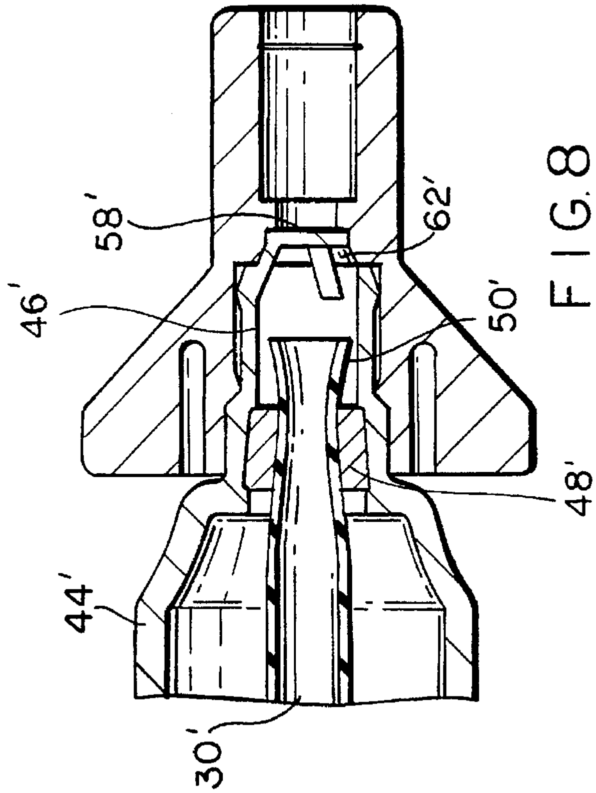
FIG. 8 is an enlarged fragmentary sectional view of the spray control valve in the closed position.

In the preferred form of spray control valve 32' shown in FIGS. 7–9, the boss 46' of handle 44' mounts the distal end 50' of hose 30' in similar fashion with a retaining ring 48'. A valve plug 58' is also provided as well as opening 62'. The valve body 52' is provided with valve seat 60' which receives the plug 58' to close the valve. Upon digitally shifting the valve body 52' forwardly the plug 58' unseats from valve seat 60 to open the valve. Reverse movement will close the valve. A sliding seal 64' is also provided which also serves to limit the extent of movement of the valve body 52'.

Thus, the several aforenoted objects and advantages are most effectively obtained. Although several somewhat preferred embodiments have been disclosed and described in detail herein, it should be understood that this invention is in no sense limited thereby and its scope is to be determined by that of the appended claims.

We claim:

1. A reusable sprayer comprising:

a tank having a top and base having an exterior and an interior for liquid to be dispensed;

an inlet at the tank top for filling the tank with liquid;

an outlet at the tank top for the liquid contained in the tank;

pump means for forcing the liquid out the outlet under pressure;

a hose having a proximal end coupled with the outlet and having a distal end;

a manual spray control valve having an axis coupled with the distal end of the hose for controlling the amount of discharge of the liquid that is sprayed, the valve including a fixed valve plug and an aperture permitting liquid to bypass the plug, a valve body slidable axially relative to the plug and having a valve seat that receives the plug to close the valve and upon unseating the plug from the seat, the valve opens, the valve body having direct digitally engageable surfaces that are engaged directly by the digits for axially moving the valve body digitally relative to the fixed valve plug between the valve closed and open position, whereby the valve body is adapted to be digitally axially moved from its closed position wherein the plug seats on the valve seat and stops liquid from being discharged to its open position by digitally engaging the digitally engageable surfaces whereupon the liquid from the distal end of the hose is adapted to flow through the aperture and through the valve and be sprayed and digitally moved axially back to the closed position to stop the spray of the liquid by digitally engaging the digitally engageable surfaces.

2. The invention in accordance with claim 1 wherein a handle for grasping by an operator of the sprayer is provided and which has a distal end having a boss, the valve plug being at the distal end of the handle and the valve body being slidable on the distal end of the handle.

3. A reusable sprayer comprising:

a tank having an exterior and an interior for liquid to be dispensed;

an inlet for filling the tank with the liquid;

an outlet for the liquid contained in the tank;

pump means for forcing the liquid out the outlet under pressure;

a hose having a proximal end coupled with the outlet and having a distal end;

a manual spray control valve coupled with the distal end of the hose for controlling the amount of discharge of the liquid that is sprayed, the valve including a fixed valve plug and an aperture permitting liquid to bypass the plug, a valve body slidable relative to the plug and having a valve seat that receives the plug to close the valve and upon unseating the plug from the seat, the valve opens, whereby the valve body is adapted to be digitally moved from its closed position wherein the plug seats on the valve seat and stop liquid from being discharged to its open position whereupon the liquid from the distal end of the hose is adapted to flow through the aperture and through the valve and be sprayed and moved back to the closed position to stop the spray of the liquid;

a handle for grasping by an operator of the sprayer being provided and which has a distal end having a boss, the valve plug being at the distal end of the handle and the valve body being slidable on the distal end of the handle;

the boss including an internal through opening, a retainer ring being in the through opening for clamping the distal end of the hose.

4. The invention in accordance with claim 2 wherein the valve plug is separate and is mounted within the boss.

5. The invention in accordance with claim 2 wherein the valve plug forms an integral part of the boss.

6. The invention is accordance with claim 1 wherein the valve body has a distal end, and an extension rod is coupled with the distal end of the valve body.

7. The invention in accordance with claim 6 wherein the extension rod has a distal end and a discharge nozzle is at the distal end of the extension rod.

8. The invention in accordance with claim 1 where an angled handle extends upwardly and integrally from the tank and is so constructed and arranged so that when gripped, the tank will tilt to permit all of the liquid in the tank to be removed by spraying.

9. The invention in accordance with claim 1 wherein a longitudinal cavity is formed on the exterior of the tank, an extension rod is coupled with the discharge nozzle and the rod being disposed in the cavity and secured therein prior to purchase and use thereof by a customer.

10. The invention in accordance with claim 1 wherein the tank has a base, a reverse dome integrally molded in the base for strengthening the base and prevent ballooning thereof.

11. The invention in accordance with claim 1 wherein the exterior of the tank is slightly recessed about its circumference to receive a shrink wrapped label.

* * * * *

UNITED STATES PATENT AND TRADEMARK OFFICE

CERTIFICATE OF CORRECTION

PATENT NO. : 5,649,664

DATED : Jul. 22, 1997

INVENTOR(S) : Richard Brass, Raymond F. Cracauer, Roland Beihl, Robert C. Hudson, Jr.

It is certified that error appears in the above-identified patent and that said Letters Patent is hereby corrected as shown below:

Column 2, line 67, "60" should read --60'--.

Signed and Sealed this

Eleventh Day of November, 1997

Attest:

BRUCE LEHMAN

*Attesting Officer* *Commissioner of Patents and Trademarks*